(12) United States Patent
Deflorian et al.

(10) Patent No.: US 11,793,903 B2
(45) Date of Patent: Oct. 24, 2023

(54) FRAGRANCE DIFFUSER DEVICE WITH AN END-OF-LIFE INDICATOR, FOR USE ONTO MOTOR VEHICLE VENTILATION GRIDS

(71) Applicant: ZOBELE HOLDING S.P.A., Trento (IT)

(72) Inventors: Stefano Deflorian, Trento (IT); Stefano Baldessari, Trento (IT)

(73) Assignee: ZOBELE HOLDING S.P.A., Trento (IT)

( * ) Notice: Subject to any disclaimer, the term of this patent is extended or adjusted under 35 U.S.C. 154(b) by 470 days.

(21) Appl. No.: 16/760,584

(22) PCT Filed: Oct. 29, 2018

(86) PCT No.: PCT/IB2018/058446
§ 371 (c)(1),
(2) Date: Apr. 30, 2020

(87) PCT Pub. No.: WO2019/087036
PCT Pub. Date: May 9, 2019

(65) Prior Publication Data
US 2020/0345883 A1  Nov. 5, 2020

(30) Foreign Application Priority Data
Oct. 30, 2017 (IT) .................. 102017000123395

(51) Int. Cl.
*A61L 9/12* (2006.01)
(52) U.S. Cl.
CPC .......... *A61L 9/12* (2013.01); *A61L 2209/133* (2013.01); *A61L 2209/15* (2013.01)

(58) Field of Classification Search
None
See application file for complete search history.

(56) References Cited

U.S. PATENT DOCUMENTS

| | | |
|---|---|---|
| 6,264,887 B1 | 7/2001 | Farmer |
| 8,460,609 B1 | 6/2013 | Wheatley et al. |
| 8,685,330 B2 | 4/2014 | Irvin et al. |
| 9,155,812 B1 | 10/2015 | Bourne |
| 9,314,543 B2 | 4/2016 | Bourne |

(Continued)

FOREIGN PATENT DOCUMENTS

| | | |
|---|---|---|
| EP | 3135303 A1 | 3/2017 |
| ES | 1057369 U | 7/2004 |

OTHER PUBLICATIONS

Dictionary.com—"Window"—definition. pp. 1-5. https://www.dictionary.com/browse/window (Year: 2023).*

(Continued)

*Primary Examiner* — Jelitza M Perez
(74) *Attorney, Agent, or Firm* — NIXON & VANDERHYE

(57) ABSTRACT

A fragrance diffuser device for motor vehicle interiors, of the type including an elongated support body, a refill of a fragrance-impregnated plastic material fixed to a fastening base of the support body, and an elastic clamp to hook the diffuser onto a motor vehicle ventilation system grid. The fastening base consists of a rib longitudinally extending for at least part of the support body length and retaining by friction the refill of a fragrance-impregnated plastic material which at least partially surrounds the rib.

20 Claims, 3 Drawing Sheets

(56) References Cited

U.S. PATENT DOCUMENTS

| | | | |
|---|---|---|---|
| 9,833,534 B2 | 12/2017 | D'Amico | |
| 10,391,192 B2 | 8/2019 | D'Amico | |
| 2010/0065654 A1* | 3/2010 | Wheatley | ............... A61L 9/042 |
| | | | 239/56 |
| 2013/0341424 A1 | 12/2013 | Brandenburg et al. | |
| 2018/0009293 A1* | 1/2018 | Quintanar | ............... B60H 3/00 |

OTHER PUBLICATIONS

International Search Report and Written Opinion, dated Mar. 6, 2019, from corresponding PCT application No. PCT/IB2018/058446.

* cited by examiner

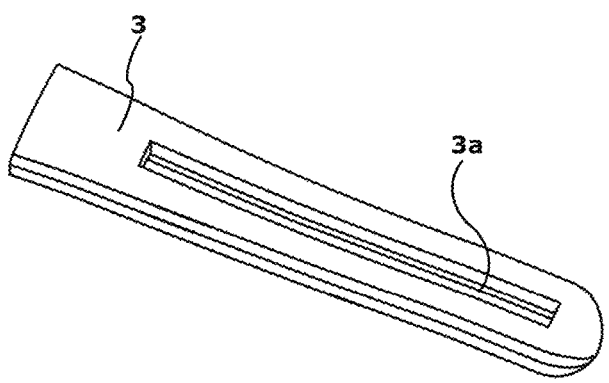
Fig. 4
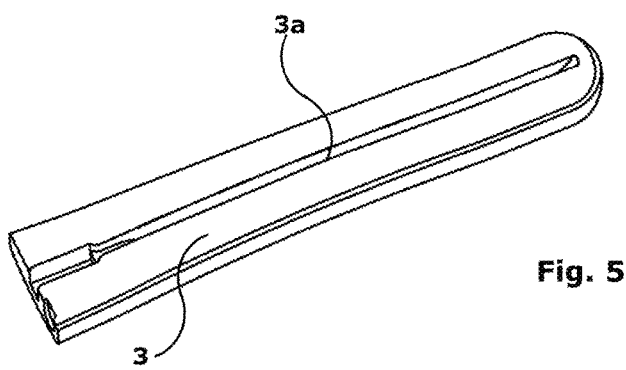
Fig. 5
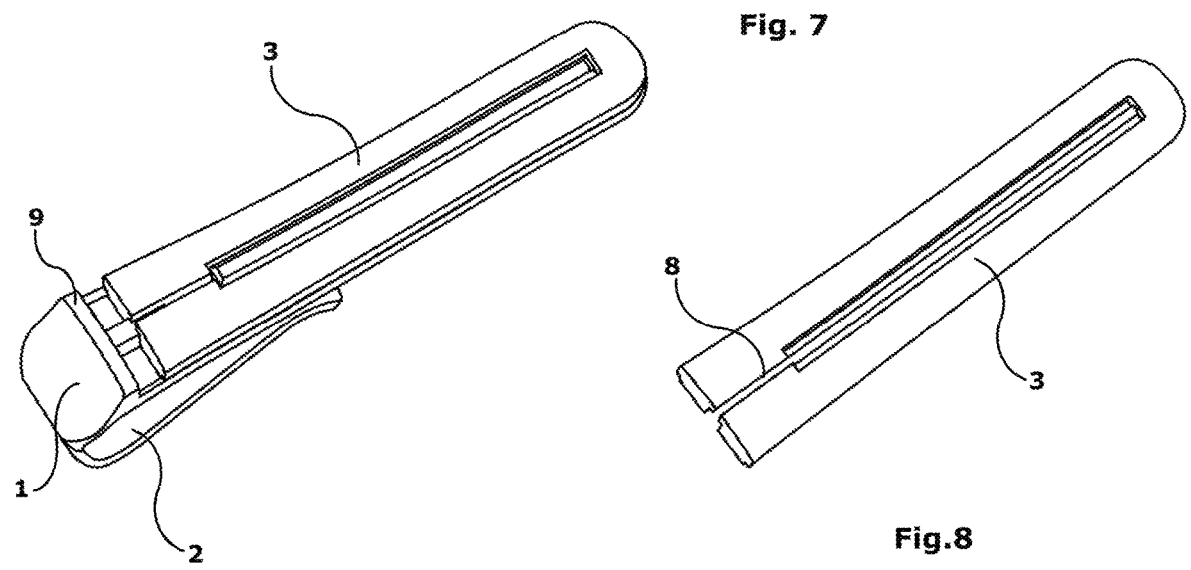
Fig. 7
Fig. 8

FRAGRANCE DIFFUSER DEVICE WITH AN END-OF-LIFE INDICATOR, FOR USE ONTO MOTOR VEHICLE VENTILATION GRIDS

FIELD OF THE INVENTION

The present invention relates to a fragrance diffuser device incorporating a plastic material impregnated with scented essences, which is intended for being used onto motor vehicle ventilation grids. The term "fragrance diffuser device", as used herein and in the following, is also intended to include a "room air freshener device", to which the present invention also refers.

BACKGROUND OF THE PRIOR ART

Fragrance diffuser devices have been known since long; particularly, the use of a diffuser consisting in a support made of a fragrance-impregnated plastic material, is well known. EVA co-polymer (ethylene-vinyl acetate), which exhibits a good flexibility feature and lends very well itself to being impregnated with a scented substance to be released into the environment during its service-life, is preferably used as a plastic material for impregnation.

To this purpose, said diffuser is widely known for being made as a shaped plate of a fragrance-impregnated plastic material to be hung in the vehicle, e.g. typically on a rear-view mirror or sun visors. Such a type of hanging object, however, has a low vaporization effectiveness and moreover it can disturb the driver by constantly oscillating under the stresses due to vehicle movements.

More recently, placing such a fragrance-impregnated diffuser in the form of a plate in close proximity of a motor vehicle ventilation grid was considered with interest, as the air which circulates in the ventilation system, thereby forcibly flowing around the diffuser, is very effective in transferring the scented essences of the fragrance throughout the motor vehicle internal volume.

U.S. Pat. No. 6,264,887 discloses for example a fragrance diffuser in the form of a U-shaped plate made of polypropylene plastic material impregnated with scented essences, whose two branches can be inserted and elastically locked into the openings of a motor vehicle ventilation grid. A drawback of this kind of device is that the plastic material of the ventilation grid may be damaged by a prolonged direct contact with said scented essences.

For this reason, more effective solutions were disclosed in several earlier documents, referred to diffusers of many and varied shapes, for example in the form of elongated pliers, as disclosed by U.S. Pat. Nos. 8,460,609, 9,155,812 and 9,314,543, or in a leaf shape as disclosed by U.S. Pat. No. 8,685,330, wherein the fragrance-impregnated plastic material (usually EVA) is fixed to the device body by coupling a plurality of holes formed in said plastic material with corresponding mushroom-head pins or other similar protrusions projecting from the device body. These solutions overcome the above-mentioned drawback of a prolonged contact between the scented substance and the vehicle grid. However, the hole-and-pin fixing system is complex, hence the relative manufacturing process cannot be easily automated.

Another solution—which is particularly interesting due to its easiness to be positioned on a motor vehicle ventilation grid—is described in US-2013/0341424, where a diffuser directly formed as an elastic clamp is disclosed, a portion of the clamp extending inside the grid while a layer of fragrance-impregnated EVA is over-moulded on all sides of its arched surface, i.e. on top, bottom and lateral sides. This arrangement, despite the ease of mounting the elastic clamp on a grid and the fact that by this way the risk of a direct contact between the fragrance-impregnated plastic material and the grid is avoided, results in at least the following drawbacks: on one hand, the EVA material over-moulding process is complex and expensive, it requires more sophisticated equipment, and thus increases the investment needed to produce such a device; on the other hand, when the scented EVA material ends its service life—because all the scented essences are evaporated—the entire device needs to be disposed, leading to obvious cost and pollution problems.

SUMMARY OF THE INVENTION

It is therefore an object of the present invention to provide a fragrance diffuser intended for use in motor vehicles and, more specifically, designed for an easy clamping on a motor vehicle ventilation grid, which has a simpler structure than those of the prior art, a more reliable clamping action on a grid, a less expensive manufacturing process, and which is suitable for a quick and easy replacement of the refills of fragrance-impregnated material.

Another object of the invention is to take advantage of the natural shrinkage of the fragrance-impregnated plastic material while the evaporation proceeds, in order to provide an indication of the consumption of the fragrance, and hence an end-of-life indication for this device.

These objects are achieved by a device having the features defined in claim 1. Further preferred features of such device are set out in the dependent claims.

BRIEF DESCRIPTION OF THE DRAWINGS

Further features and advantages of the invention will in any case become more evident from the following detailed description, given by way of non-limiting example and illustrated in the attacked drawings, wherein:

FIG. 4 is a perspective view from above of a refill of fragrance-impregnated plastic material, suitable for the first embodiment of the fragrance diffuser device according to the invention;

FIG. 5 is a perspective view from below of the refill of FIG. 4;

FIG. 7 is an overall perspective view from above of a third embodiment of the fragrance diffuser device according to the invention, provided with an elastic clamp and comprising a refill of fragrance-impregnated plastic material; and FIG. 8 is a perspective view from above of a refill of fragrance-impregnated plastic material for the third embodiment of the diffuser device according to the invention.

DETAILED DESCRIPTION OF THE PREFERRED EMBODIMENTS

Figure 1:
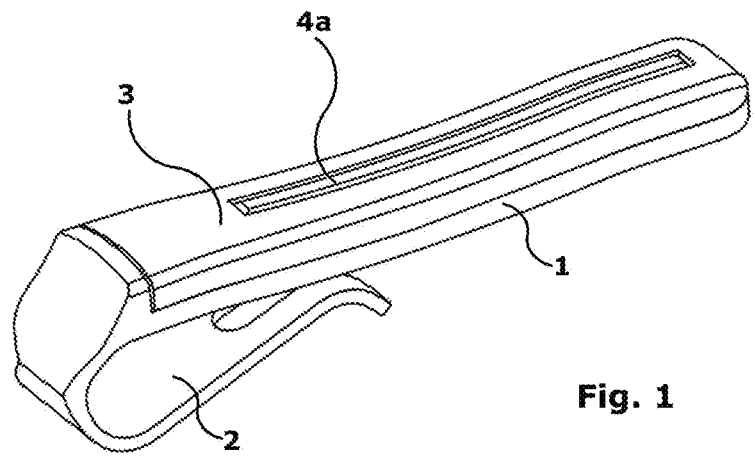
FIG. 1 is an overall perspective view from above of a first embodiment of the fragrance diffuser device according to the invention, provided with an elastic clamp and comprising a refill of fragrance-impregnated plastic material.

As illustrated in the perspective view of FIG. 1, the diffuser device according to the invention comprises an elongated support body 1, which extends downwardly from one end in the shape of a flap which forms an elastic clamp 2, suitable for clamping the device to a motor vehicle ventilation grid. The support body 1 is preferably moulded or extruded into a rigid low-cost plastic material, such as polypropylene or any other plastic material having similar mechanical characteristics. Nevertheless, support body 1 could also be made of any other material, for example a metallic or composite material. The elastic clamp 2 resilience is essentially due to the clamp arched shape and not to an intrinsic resilience of the material, which material, as above said, is essentially rigid.

A refill 3, made of a fragrance-impregnated plastic material, is meant to be engaged on support body 1, where said refill 3 is the active element of the diffuser and is shaped as an elongated parallelepiped such as to harmoniously match with the shape of support body 1. Any known polymer which can be impregnated with scented essences mixtures can be used as the plastic material, such as polyurethanes, polyether block amides, silicones or preferably ethylene vinyl acetate copolymers (EVA). For the sake of brevity, exclusive reference will be made in the following to EVA, being intended that any other material having similar features can be used without departing from the scope of the present invention.

Figure 2:
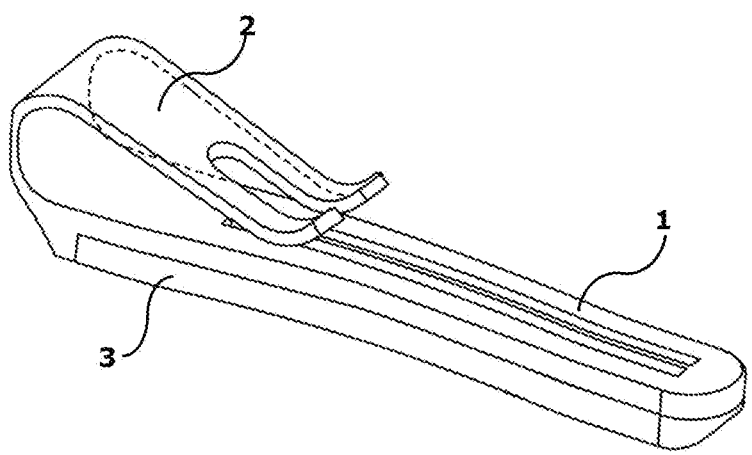
FIG. 2 is an overall perspective view from below of the device of FIG. 1.

When refill 3 is applied to support body 1, the assembly looks as shown in FIGS. 1 and 2. As can be understood from the drawing, the assembly of support body 1 and refill 3 has a thin, elongated shape, perfectly suitable to be inserted in one of the openings of a motor vehicle ventilation grid. Once this insertion operation is completed, the elastic clamp 2 can easily be hooked onto one of the grid cross-pieces, as already discloses in the prior art closest to the invention, namely the aforementioned document US-2013/0341424.

According to a first feature of the invention, refill 3 is interchangeably applied on support body 1. Thanks to this way, support body 1 can be used indefinitely, providing to replace the refill 3 when its scenting function is ended.

In order to quickly and practically achieve this object, support body 1 is formed by a slightly hollow base bounded by a small edge 5, and suitably sized for housing the refill 3; in addition to this an elongated rib 4 perpendicularly projects from the bottom of that base and along its centre axis, extending for a portion of the support body 1 and retaining the refill 3. To this purpose refill 3 is provided, in fact, with an axial cut-out 3a, which is substantially equal or only slightly smaller in size than said rib 4; this way, the cut-out 3a of refill 3 can be elastically inserted onto rib 4 so that refill 3 is frictionally retained on the support body 1, also matching within the hollow base thereof, bounded by the small edge 5.

Figure 3:
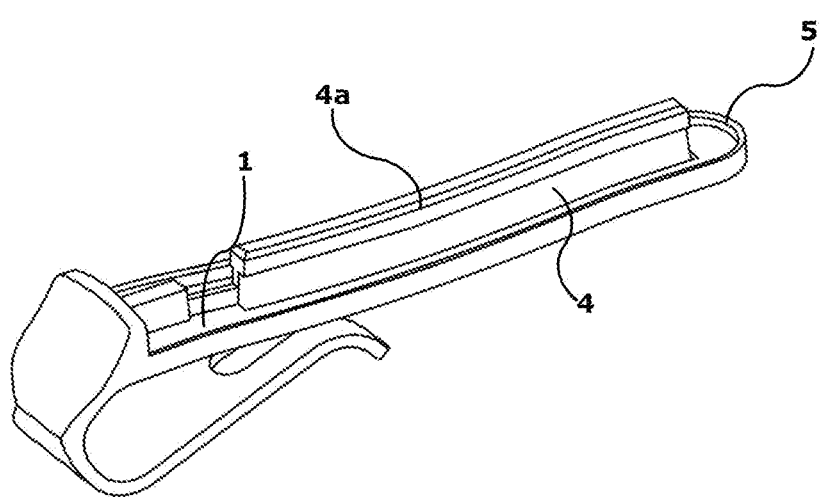
FIG. 3 is a perspective view similar to FIG. 1 of the diffuser base body alone, without the refill of fragrance-impregnated plastic material.

As can easily be seen from FIG. 3, in order to improve the refill 3 retention, rib 4 is preferably formed with its upper edge 4a slightly widened, so that a slight forcing on the cut-out 3a opening is required in order to overcome edge 4a, when cut-out 3a is inserted on the rib 4, so that refill 3 is eventually pressure wedged on rib 4 and retained therein. This construction safely prevents that refill 3 may accidentally slip out of the support body 1 and into a motor vehicle ventilation grid during manipulation and insertion onto said ventilation grid of the device according to the invention.

Even though insertion of the cut-out 3 on the widened edge 4a can be obtained taking advantage of the elastic nature of the plastic material of refill 3, an alternative embodiment is also possible wherein the shape of the upper edge 4a of rib 4 is complementarily provided in the cut-out 3a of refill 3, so that said two elements mutually match upon mutual insertion, without refill 3 having to remain elastically deformed on rib 4.

In the embodiment of FIGS. 1 to 5, rib 4 covers almost the entire length of support body 1, close to both its opposite ends. Consequently, refill 3 also is substantially as long as body 1 and cut-out 3a extends in its centre portion without involving its end portions.

As it is easily understood, this arrangement allows the refill 3 according to the invention to be extremely simple and inexpensive, as well as being easily interchangeable, so as to allow multiple use of the support body 1.

According to another feature of the fragrance diffuser according to the present invention, refill 3 arrangement allows to provide an indication of the degree of consumption of the fragrance diffuser itself. To obtain this indication, the present invention relies on the observation that refill 3—generally consisting of a plastic material, such as EVA, impregnated with scented essences—undergoes a volume reduction and therefore a dimensional shrinking as said essences evaporate. Such a shrinking is obviously visible to a greater extent on the longitudinal dimension of refill 3 and it is therefore possible to use this longitudinal shrinking of refill 3 to make clear to the user the time when a replacement of the refill with a new one is necessary, by suitably modifying the support—with respect to what is known in the art—so that refill 3 can have a longitudinal, at least partial, degree of freedom.

In the first embodiment of the present invention, rib 4 retains the refill in a fixed position; consequently, as the scented essences evaporate, a shrinking of the refill 3 opposite free ends occurs, which can be measured on a graduated reference scale, for example at the diffuser end provided with the elastic clamp 2.

Figure 6A:
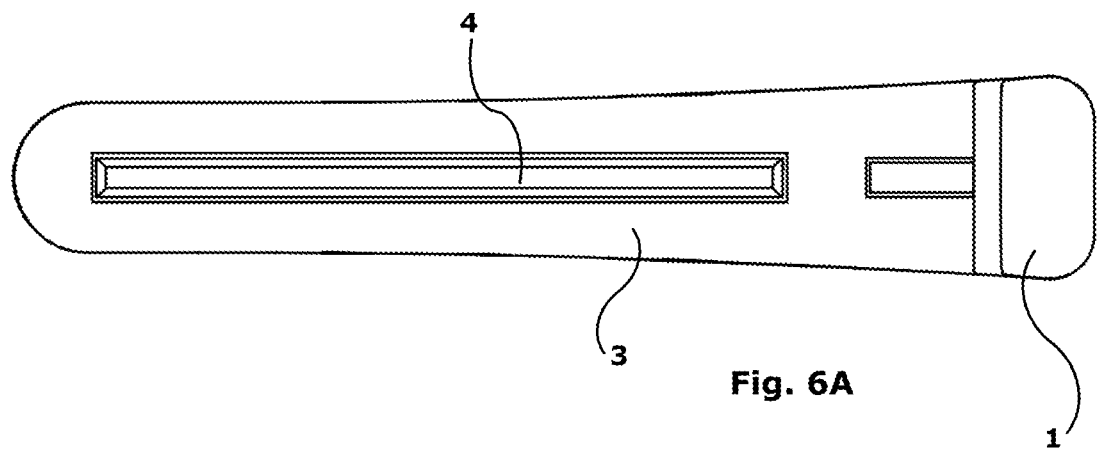
FIGS. 6A, 6B and 6C are plan views of a second embodiment of the diffuser according to the invention, showing subsequent time steps, as the scented essence evaporation continues, of the useful life of the refill of fragrance-impregnated plastic material.
Figure 6B:
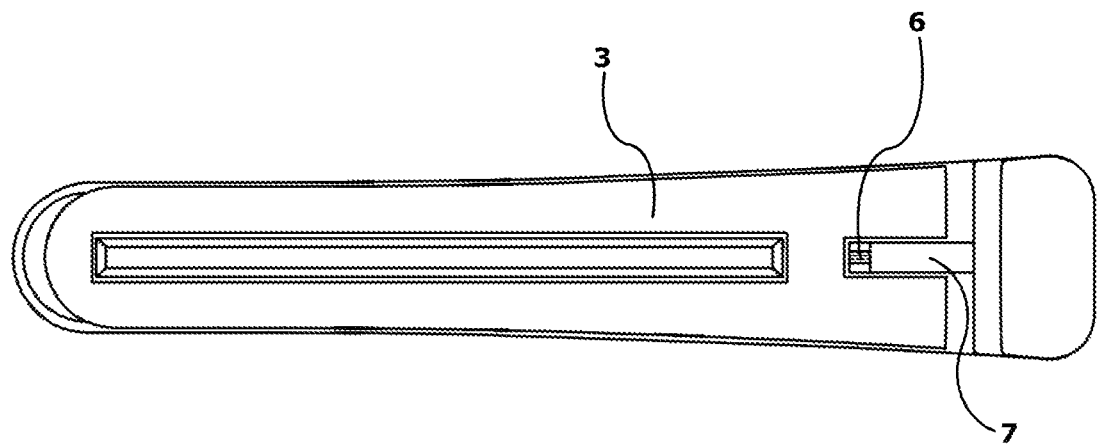
Figure 6C:
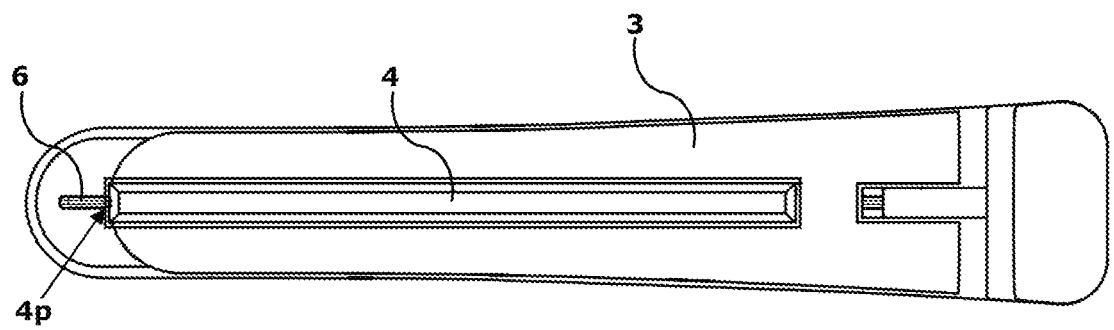

In another more apparent embodiment, schematically illustrated in FIG. 6, the two free ends of refill 3 can be made so as to have a different mutual thickness and thus a different mechanical resistance. In this case, during its service life the fragrance diffuser refill 3 undergoes the following transformations:

- FIG. 6a shows a first step, wherein refill 3 is intact, thus occupying the whole base surface of support body 1;
- FIG. 6b shows an intermediate step, wherein the scented essences evaporation causes a partial shrinking of refill 3. It can be noted, in fact, that refill 3 became shorter than support body 1 base and leaves now free the end zones of the same; in particular, it can be noted that two consumption indicators became visible at the two opposite ends of the support body 1 base, which indicators for example comprise coloured dots or stripes 6. Such dots or stripes 6 have the purpose of signalling a first partial exhaustion of refill 3, similarly to what previously discussed in relation to the first embodiment of the present invention;
- FIG. 6c finally shows the final step of use of refill 3, wherein the progressive shrinking of the refill 3 caused an internal stress thereof, at the opposite ends of rib 4, until tearing of its thinner end. This tearing action, possibly aided by a sharp shape of the end 4p of rib 4, provides a highly visible consumption indicator which warns the users about the need to replace refill 3. As can be understood by the drawings, in this embodiment it is also possible to provide for the refill 3 larger end having a central terminal cut-out matching with a second rib 7, which has the only purpose of retaining in the right position, i.e. without lateral twisting, the corresponding end of refill 3 during the use and therefore the progressive shrinking of the refill itself.

According to a further alternative arrangement, illustrated in FIGS. 7 and 8, means are provided to maintain one of the refill 3 ends fixed to base body 1, therefore allowing refill 3 to freely shrink on its whole length. This way, he overall extent of shrinking increases and its measurement becomes thus easier.

To this end, refill 3 can be made, for example, in a U-shape, the U recess being formed by cut-out 3a which embraces rib 4 and extends beyond it into a slit 8 which bisects one of the refill 3 ends; in other words, refill 3 would be provided with a longitudinal cut-out 3a which is closed only at one of its ends, and therefore would only partially extend around rib 4.

Fixing of refill 3 is thus provided only at the closed end of cut-out 3a, i.e. at the base of the U-shape; therefore, during the product service-life, the refill 3 end where cut-out 3a is open could shrink freely, progressively decreasing the refill length, thus indicating the product remaining life. For an immediate detection, a sign or another fixed reference could be provided in the base body 1, in order to signal to the user that, when this sign is visible, the product must be replaced with a new one, or to indicate, in days, the expected remaining service-life. In the illustrated embodiment, the shortening becomes readily visible thanks to the fact that an empty zone of increasing width is formed between the open end of the U-shaped refill 3 and the opposite wall 9 of the support body 1, as clearly illustrated in FIG. 7. As it is when looking at FIG. 7, in this embodiment the central rib 4 extends up to the wall 9, through the open end of the U-shaped refill 3, thus providing lateral stability thereto.

These different embodiments of the diffuser device of the invention can also be used depending on their different way to be clamped on a motor vehicle ventilation grid. It is clear, in fact, that the fragrance diffuser device needs to be clamped in the best exposure with respect to the air flow, in order to achieve a correct evaporation efficacy.

In any case, the diffuser support body 1 is not completely entered into the ventilation system grid but at least one of its ends remains outside the grid. This enables to easily control the refill consumption without any need to remove the elastic clamp 2 from the opening of the grid wherein it was clamped.

In order to increase the ventilation air flow around refill 3, it may be useful to form in the support body 1 base one or more ventilation cut-outs, arranged for example parallel to the central rib 4 and through the entire thickness of support body 1.

However, it is to be understood that the fragrance diffuser of the present invention is not limited to the particular embodiments illustrated above, which are intended to provide only non-limiting examples of the invention, but that several variants are possible, within the reach of those skilled in the art, which variants still fall within the scope of the invention which is only defined by the appended claims.

The invention claimed is:

1. A fragrance diffuser for motor vehicle interiors, the fragrance diffuser comprising:
an elongated support body comprising a fastening base;
a refill of a fragrance-impregnated plastic material fixed to the fastening base of said support body; and
an elastic clamp to hook the diffuser onto a motor vehicle ventilation system grid,
wherein said fastening base comprises a rib longitudinally extending for at least two-thirds of said support body longitudinal length and retaining by friction said refill of a fragrance-impregnated plastic material,
wherein said refill at least partially surrounds said rib and is provided with an axial cut-out configured to receive the rib such that the refill is frictionally retained by the rib,
wherein said axial cut-out is longitudinally extending and defined within the refill along a longitudinal length of the refill, and
wherein said refill has a longitudinal degree of freedom.

2. The fragrance diffuser of claim 1, wherein an upper edge of said rib is widened relative to the thickness of the rib itself.

3. The fragrance diffuser of claim 1, wherein said refill is shaped as a parallelepiped and extends for at least part of said support body longitudinal length.

4. The fragrance diffuser of claim 3, wherein said longitudinal axial cut-out is closed at both opposite ends thereof.

5. The fragrance diffuser of claim 3, wherein said axial cut-out is open at one end thereof and said refill is U-shaped.

6. The fragrance diffuser of claim 1, wherein said rib and said axial cut-out have matching profiles allowing mutual engagement therebetween.

7. The fragrance diffuser of claim 1, wherein said elongated support body further comprises a consumption indicator of said refill, the consumption indicator becoming visible only after said refill shrinks due to exhaustion of said fragrance.

8. The fragrance diffuser of claim 7, wherein at least one end of said refill is free to shrink upon evaporation of the fragrance and said consumption indicator consists of colored striped or dots which are provided on the fastening base of said elongated support body and become visible due to the refill shrinking.

9. The fragrance diffuser of claim 7, wherein one end of said rib prevents at least one end of said refill from shrinking upon evaporation of the fragrance, and said consumption indicator consists in breakage of said refill end, caused by local stresses which take place in the refill at said rib end, as a result of said fragrance evaporation.

10. The fragrance diffuser of claim 9, wherein said one end of said rib has a sharp profile to ease the breakage of one of the ends of said refill.

11. The fragrance diffuser of claim 1, wherein said refill is made of plastic materials configured to be impregnated with scented essences mixtures.

12. The fragrance diffuser of claim 1, wherein said refill made of the fragrance-impregnated plastic material is elastically and interchangeably mounted on said rib.

13. The fragrance diffuser of claim 2, wherein said refill is shaped as an elongated parallelepiped and extends for at least part of said support body longitudinal length.

14. The fragrance diffuser of claim 2, wherein said rib and said axial cut-out have matching profiles allowing mutual engagement therebetween.

15. The fragrance diffuser of claim 3, wherein said rib and said axial cut-out have matching profiles allowing mutual engagement therebetween.

16. The fragrance diffuser of claim 4, wherein said rib and said axial cut-out have matching profiles allowing mutual engagement therebetween.

17. The fragrance diffuser of claim 5, wherein said rib and said axial cut-out have matching profiles allowing mutual engagement therebetween.

18. The fragrance diffuser of claim 2, wherein said support body further comprises a consumption indicator of said refill, the consumption indicator becoming visible only after said refill shrinks due to exhaustion of said fragrance.

19. The fragrance diffuser of claim 3, wherein said support body further comprises a consumption indicator of said refill, the consumption indicator becoming visible only after said refill shrinks due to exhaustion of said fragrance.

20. The fragrance diffuser of claim 4, wherein said support body further comprises a consumption indicator of said refill, the consumption indicator becoming visible only after said refill shrinks due to exhaustion of said fragrance.

* * * * *